US012435319B2

(12) United States Patent
Sun et al.

(10) Patent No.: US 12,435,319 B2
(45) Date of Patent: Oct. 7, 2025

(54) DOUBLE TAGGED SERRATIA MARCESCENS NUCLEASE

(71) Applicant: ABclonal Science, Inc., Woburn, MA (US)

(72) Inventors: Dapeng Sun, Lexington, MA (US); Aine Quimby, Newburyport, MA (US); Zhenyu Zhu, Lynnfield, MA (US)

(73) Assignee: AbClonal Science, Inc., Woburn, MA (US)

( * ) Notice: Subject to any disclaimer, the term of this patent is extended or adjusted under 35 U.S.C. 154(b) by 470 days.

(21) Appl. No.: 18/102,841

(22) Filed: Jan. 30, 2023

(65) Prior Publication Data

US 2024/0279626 A1 Aug. 22, 2024

(51) Int. Cl.
*C12N 9/16* (2006.01)
*C08B 37/08* (2006.01)

(52) U.S. Cl.
CPC .............. *C12N 9/16* (2013.01); *C08B 37/003* (2013.01); *C12Y 301/30002* (2013.01)

(58) Field of Classification Search
CPC ..... C12N 9/16; C12N 9/22; C12Y 301/30002
See application file for complete search history.

(56) References Cited

U.S. PATENT DOCUMENTS

| | | | |
|---|---|---|---|
| 10,920,202 B1 * | 2/2021 | Zhu ................ | C12Y 301/30002 |
| 10,947,518 B1 | 3/2021 | Zhu et al. | |
| 11,020,474 B1 | 6/2021 | Xiang et al. | |
| 2020/0283825 A1 | 9/2020 | Zhu et al. | |
| 2020/0291455 A1 | 9/2020 | Zhu et al. | |
| 2020/0362320 A1 | 11/2020 | Zhu et al. | |
| 2021/0079365 A1 | 3/2021 | Zhu et al. | |
| 2021/0087550 A1 | 3/2021 | Zhu et al. | |
| 2021/0171925 A1 | 6/2021 | Zhu et al. | |
| 2021/0403537 A1 | 12/2021 | Xiang et al. | |
| 2022/0064266 A1 | 3/2022 | Xiang et al. | |
| 2022/0106576 A1 | 4/2022 | Zhu et al. | |
| 2023/0033390 A1 | 2/2023 | Xiang | |
| 2023/0094503 A1 | 3/2023 | Zhu et al. | |
| 2023/0111383 A1 | 4/2023 | Zhu et al. | |
| 2023/0212550 A1 | 7/2023 | Zhu et al. | |
| 2023/0257724 A1 * | 8/2023 | Mandell ......... | C12Y 301/21001 435/196 |
| 2023/0265412 A1 | 8/2023 | Zhu et al. | |
| 2023/0295707 A1 | 9/2023 | Zhu et al. | |
| 2024/0052326 A1 | 2/2024 | Zhu et al. | |
| 2024/0067951 A1 | 2/2024 | DiCicco et al. | |
| 2024/0124854 A1 | 4/2024 | Zhu et al. | |
| 2024/0247246 A1 | 7/2024 | Sun et al. | |
| 2024/0279626 A1 | 8/2024 | Sun et al. | |
| 2024/0392264 A1 | 11/2024 | Zhu et al. | |
| 2024/0392267 A1 | 11/2024 | Zhu et al. | |
| 2024/0392276 A1 | 11/2024 | Sun et al. | |
| 2024/0392336 A1 | 11/2024 | Sun et al. | |
| 2025/0051739 A1 | 2/2025 | Zhu et al. | |
| 2025/0223574 A1 | 7/2025 | Zhu et al. | |
| 2025/0236860 A1 | 7/2025 | Sun et al. | |

* cited by examiner

*Primary Examiner* — Tekchand Saidha
(74) *Attorney, Agent, or Firm* — Eric P. Mirabel

(57) ABSTRACT

Either wild type or mutant *Serratia marcescens* Nuclease ("SMN") is engineered to display a C-terminal Chitin Binding Domain (CBD-tag), followed, at the C-terminus side of the CBD-tag, by a poly-histidine tag (His-tag), where the His-tag is preferably a 6-mer and preferably is preceded by a Gly-Ser linker, thereby generating a recombinant SMN protein that retains dual affinity tags (a CBD-tag and a His-tag) at the C-terminus, to make it easily removed from a reaction solution following digestion of nucleic acids in the reaction mixture. It can also be used for binding SMN to a solid support for use in nucleic acid digestion in a sample contacted with the solid support.

1 Claim, 3 Drawing Sheets

Specification includes a Sequence Listing.

DOUBLE TAGGED SERRATIA MARCESCENS NUCLEASE

SEQUENCE LISTING

The instant application contains a Sequence Listing which has been submitted electronically in XML format and is hereby incorporated by reference in its entirety. Said XML copy, created on Apr. 12, 2023, is named ABCL-SMN-2TAG_SL.xml and is 4,711 bytes in size.

BACKGROUND

*Serratia marcescens* Nuclease ("SMN") (EC 3.1.30.2) is a nonspecific endonuclease capable of digesting all forms of DNA and RNA into fragments ranging from one to four 5'-phosphorylated nucleotides in length. This enzyme has high catalytic efficiency, with a specific activity measuring 1 million active units per milligram of protein. Recombinant SMN has been widely commercialized and is marketed under a variety of different names such as Benzonase from Millipore Sigma and GENIUS Nuclease by Acro Biosystems. SMN is frequently relied upon to remove contaminating nucleic acids from preparations of purified proteins.

A Chitin Binding Domain (CBD) is a polypeptide which specifically binds to N-acetyl glucosamine, derived from the small domain of the chitinase A1 gene of *Bacillus circulans*. CBD binding is nearly irreversible, making it useful in tagging proteins for purification purposes. The CBD binds tightly to chitin, which is a poly N-acetyl glucosamine and one of the most common polymers from nature. It exists in the shells of all crustaceans and insects, and also many fungi, algae, and yeast. Chitin is commercially available as resin, chitin beads, or chitin magnetic beads (New England Biolabs, Ipswich, MA). Protein that is expressed with the CBD-tag, or as a fusion protein in which the CBD is fused to the target protein, can be subjected to Chitin Purification. Proteins immobilized to chitin resin or beads via CBD-tags can be separated from crude cell lysate through affinity purification protocols. Purified protein is eluted from the CBD via chemically inducing internal cleavage between the tag and the fused protein.

Another commonly used tag in affinity chromatography is the poly-histidine tag (His-tag), which involves the addition of an uninterrupted string of four to ten histidine residues to the N- or C-terminus of a target protein. His-tagged proteins bind to immobilized metal ions in carriers such as resin or magnetic beads. Bound protein can be eluted after purification using increasing concentrations of imidazole, which competes with the target protein for binding with the metal ions, displacing purified protein into solution for recovery.

To date, a combination of the CBD-tag in conjunction with a 6-mer His tag has not been used to purify SMN in a protocol that retains both the His-tag and the CBD-tag after purification. Purification of this double-tagged SMN relies primarily on the 6-mer His tag.

SMN is primarily used to degrade contaminating nucleic acids during purification and preparation of other target proteins. Many applications require the removal of SMN after it has completed this purpose, especially if the target protein will be used to manipulate nucleic acids (i.e. DNA or RNA polymerase, DNA Ligase, RNA reverse transcriptase, DNA restriction enzymes, or others). Any SMN remaining in those purifications meant for later use with nucleic acid would interfere with the action of those purified enzymes. Thus, reliable methods to remove SMN from a reaction mixture, or bind it to solid supports to use in digestion of contaminating nucleic acids, are highly desirable.

SUMMARY

*Serratia marcescens* Nuclease (either wild type or mutant, both designated "SMN" herein) is engineered to display a C-terminal Chitin Binding Domain (CBD-tag), followed, at the C-terminus side of the CBD-tag, by a poly-histidine tag (His-tag), where the His-tag is preferably a 6-mer and preferably is preceded by a Gly-Ser linker, thereby generating a recombinant SMN protein that retains dual affinity tags (a CBD-tag and a His-tag) at the C-terminus, even after its His-tag purification.

The invention further includes recombinant SMN (wild type or mutant SMN with a CBD and a His-tag, with or without a linker) wherein the SMN portion of the recombinant SMN has an amino acid sequence with only conservative substitutions, such that the molecule has at least 70%, 80%, 90%, 95%, 96%, 97%, 98% or 99% identity to wild type SMN (hereinafter referred to as "Variant Sequences").

The invention further includes the DNA sequences encoding recombinant SMNs above and further includes the foregoing DNA sequences and other degenerate nucleic acid sequences (collectively the "Degenerate Nucleic Acid Sequences") encoding (i) each of the above recombinant SMNs, and (ii) the amino acid sequences of any of the Variant Sequences.

The invention further includes vectors incorporating any Degenerate Nucleic Acid Sequences; and cells transformed with any such vectors or Degenerate Nucleic Acid Sequences and capable of expressing any of the above recombinant SMN amino acid sequences or Variant Sequences.

The invention further includes a composition or a kit comprising any of the above recombinant SMN amino acid sequences or Variant Sequences, Degenerate Nucleic Acid Sequences, or vectors incorporating such Degenerate Nucleic Acid Sequences. The invention also includes a process of digesting a target nucleic acid, wherein any of the above recombinant SMN or Variant Sequences are employed in a reaction mixture designed to degrade a target nucleic acid, and subjecting the reagent mixture to conditions for degradation of the target nucleic acid.

The invention further includes using immobilized chitin or beads having metal ions (including magnetic beads) to remove recombinant SMN from a reaction solution, after nucleic acid digestion. The recombinant SMN bound to chitin beads or resin via the CBD, or to metal ion beads through the histidine tag, can also be used repeatedly to cleave nucleic acids in samples, for example, by placement in a column, or by using magnetic beads in the reaction solution which are thereafter attracted and removed.

DETAILED DESCRIPTION

Figure 1:
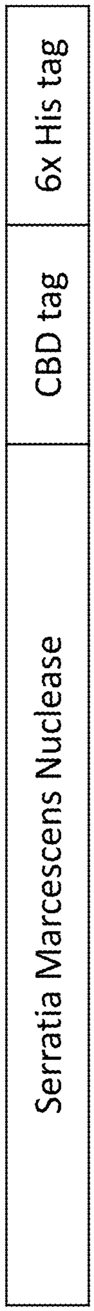
FIG. 1: The schematic structure of recombinant SMN (*Serratia marcescens* Nuclease) having an added CBD/6-mer His-tag, with the SMN at the N-terminus, CBD in the middle, and the 6-mer His-tag at the C-terminus.

Either wild type or mutant SMN is engineered to display an C-terminal Chitin Binding Domain tag (CBD-tag), followed by a C-terminal 6-mer poly-histidine tag (His-tag) (which is preferably preceded by a Gly-Ser linker), generating recombinant SMN, that retains dual affinity tags (His-tag and CBD-tag) at the C-terminus, even after His-tag purification.

The term "biologically active fragment" refers to any fragment, derivative, homolog or analog of a recombinant SMN or Variant Sequences (defined below) that possesses in vivo or in vitro activity that is characteristic of wild type SMN. In some embodiments, the biologically active fragment, derivative, homolog or analog of the recombinant SMN possesses any degree of the biological activity of the wild type or mutant SMN in any in vivo or in vitro assay.

In some embodiments, the biologically active fragment can optionally include any number of contiguous amino acid residues of the recombinant SMN or Variant Sequences. The invention also includes the polynucleotides encoding any such biologically active fragment or Variant Sequences.

Biologically active fragments can arise from post transcriptional processing or from translation of alternatively spliced RNAs, or alternatively can be created through engineering, bulk synthesis, or other suitable manipulation. Biologically active fragments include fragments expressed in native or endogenous cells as well as those made in expression systems such as, for example, in bacterial, yeast, plant, insect or mammalian cells.

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) supra). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

When referring to a gene, "mutant" means the gene has at least one base (nucleotide) change, deletion, or insertion with respect to a native or wild type gene. The mutation (change, deletion, and/or insertion of one or more nucleotides) can be in the coding region of the gene or can be in an intron, 3' UTR, 5' UTR, or promoter region. As nonlimiting examples, a mutant gene can be a gene that has an insertion within the promoter region that can either increase or decrease expression of the gene; can be a gene that has a deletion, resulting in production of a nonfunctional protein, truncated protein, dominant negative protein, or no protein; or, can be a gene that has one or more point mutations leading to a change in the amino acid of the encoded protein or results in aberrant splicing of the gene transcript.

The terms "recombinant SMN" when used in this Detailed Description section refer to, depending on the context, collectively or individually, a recombinant wild type or mutant SMN with CBD and His tags, including the mutant in SEQ ID NO: 2 with tags added, and wild type or other SMN mutants tagged with CBD and histidine, similar to the exemplary embodiment shown and described herein, as well as Variant Sequences, and Degenerate Nucleic Acid Sequences refers to any nucleic acid sequences encoding any recombinant SMN, including SEQ ID NO:1.

"Wild-type" refers to the form found in nature. For example, a naturally occurring or wild-type SMN is a sequence present in an organism, which has not been intentionally modified by human manipulation.

The terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), Nature Genetics 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), Proc. Natl. Acad. Sci. USA 89, 10915-10919), recommended for query sequences over 85 units in length (nucleotide bases or amino acids).

In some embodiments, the invention relates to methods (and related kits, systems, apparatuses and compositions) for performing a digestion reaction comprising or consisting of contacting a recombinant SMN or a biologically active fragment thereof with a polynucleotide for digestion by the recombinant SMN or the biologically active fragment thereof.

Making Recombinant SMN

The recombinant SMN of the invention can be expressed in any suitable host system, including a bacterial, yeast, fungal, baculovirus, plant or mammalian host cell. For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proc. Natl Acad. Sci. USA 75: 3727-3731), as well as the tac promoter (DeBoer et al., 1983, Proc. Natl Acad. Sci. USA 80: 21-25).

For filamentous fungal host cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-488.

For baculovirus expression, insect cell lines derived from Lepidopterans (moths and butterflies), such as *Spodoptera frugiperda*, are used as host. Gene expression is under the control of a strong promoter, e.g., pPolh.

Plant expression vectors are based on the Ti plasmid of *Agrobacterium tumefaciens*, or on the tobacco mosaic virus (TMV), potato virus X, or the cowpea mosaic virus. A commonly used constitutive promoter in plant expression vectors is the cauliflower mosaic virus (CaMV) 35S promoter.

For mammalian expression, cultured mammalian cell lines such as the Chinese hamster ovary (CHO), COS, including human cell lines such as HEK and HeLa may be used to produce the recombinant SMN. Examples of mammalian expression vectors include the adenoviral vectors, the pSV and the pCMV series of plasmid vectors, vaccinia and retroviral vectors, as well as baculovirus. The promoters for cytomegalovirus (CMV) and SV40 are commonly used in mammalian expression vectors to drive gene expression. Non-viral promoters, such as the elongation factor (EF)-1 promoter, are also known.

The control sequence for the expression may also be a suitable transcription terminator sequence, that is, a sequence recognized by a host cell to terminate transcription. The terminator sequence is operably linked to the 3' terminus of the nucleic acid sequence encoding the polypeptide. Any terminator which is functional in the host cell of choice may be used.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase.

Terminators for insect, plant and mammalian host cells are also well known.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiol Rev 57: 109-137.

Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells can be from the genes for *Saccharomyces cerevisiae* alpha-factor and *Saccharomyces cerevisiae* invertase. Signal peptides for other host cell systems are also well known.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the recombinant SMN relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter. Regulatory systems for other host cells are also well known.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the KRED polypeptide of the present invention would be operably linked with the regulatory sequence.

Another embodiment includes a recombinant expression vector comprising a polynucleotide encoding an engineered recombinant SMN or a variant thereof, and one or more expression regulating regions such as a promoter and a terminator, and a replication origin, depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the recombinant SMN at such sites. Alternatively, the nucleic acid sequences of the recombinant SMN may be expressed by inserting the nucleic acid sequences or a nucleic acid construct comprising the sequences into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the recombinant SMN polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon, may be used.

The expression vector herein preferably contain one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*. Selectable markers for insect, plant and mammalian cells are also well known.

The expression vectors of the present invention preferably contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location (s) in the chromosome(s). The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A ori, or the origins of replication of plasmids pBR322, pUC19, pACYC177 (which plasmid has the P15A ori), or pACYC184 permitting replication in *E. coli*, and pUB110, pE194, pTA1060, or pAM31 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it's functioning temperature-sensitive in the host cell (see, e.g., Ehrlich, 1978, Proc Natl Acad Sci. USA 75:1433).

More than one copy of a nucleic acid sequence of the recombinant SMN may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Expression vectors for the recombinant SMN polynucleotide are commercially available. Suitable commercial expression vectors include p3×FLAG™ expression vectors from Sigma-Aldrich Chemicals, St. Louis Mo., which includes a CMV promoter and hGH polyadenylation site for expression in mammalian host cells and a pBR322 origin of replication and ampicillin resistance markers for amplification in *E. coli*. Other suitable expression vectors are pBluescriptII SK(−) and pBK-CMV, which are commercially available from Stratagene, LaJolla Calif., and plasmids which are derived from pBR322 (Gibco BRL), pUC (Gibco BRL), pREP4, pCEP4 (Invitrogen) or pPoly (Lathe et al., 1987, Gene 57:193-201).

Suitable host cells for expression of a polynucleotide encoding the recombinant SMN, are well known in the art and include but are not limited to, bacterial cells, such as *E. coli, Lactobacillus kefir, Lactobacillus brevis, Lactobacillus minor, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art. Polynucleotides for expression of the recombinant SMN may be introduced into cells by various methods known in the art. Techniques include among others, electroporation, biolistic particle bombardment, liposome mediated transfection, calcium chloride transfection, and protoplast fusion. Various methods for introducing polynucleotides into cells are known to the skilled artisan.

Polynucleotides encoding the recombinant SMN can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides can be prepared by chemical synthesis using, e.g., the classical phosphoramidite method described by Beaucage et al., 1981, Tet Lett 22:1859-69, or the method described by Matthes et al., 1984, EMBO J. 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources, such as The Midland Certified Reagent Company, Midland, Tex., The Great American Gene Company, Ramona, Calif., ExpressGen Inc. Chicago, Ill., and Operon Technologies Inc., Alameda, Calif.

The recombinant SMN expressed in a host cell can be recovered from the cells and or the culture medium using any one or more of the well-known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available under the trade name CelLytic B™ from Sigma-Aldrich of St. Louis Mo.

Chromatographic techniques for isolation of the recombinant SMN include, among others, reverse phase chromatography high performance liquid chromatography, ion exchange chromatography, gel electrophoresis, and affinity chromatography. Conditions for purification will depend, in part, on factors such as net charge, hydrophobicity, hydrophilicity, molecular weight, molecular shape, and will be apparent to those having skill in the art. Chitin bound to resin or beads, or metal ion beads, or magnetic beads, could also be used for the purification of recombinant SMN.

The example below shows making and using of one example of a recombination SMN of the invention.

Example

The SMN herein may be wild type or one of any of several functional mutants. The SMN described in the experiments described here is the SMN mutant shown in U.S. patent Ser. No. 10/920,202B1 (incorporated by reference). This mutant has the mutations at R146D/D156R/D221R/D245R. The DNA sequence (SEQ ID NO: 1) encodes the protein shown in FIG. 1, where the mutant SMN is near the N-terminus, followed by the CBD-tag and then a 6-mer His-tag. Linkers such as Gly-Ser sequences may be used between the tags. The DNA sequence is shown in SEQ ID NO:1 below.

```
SEQ ID NO: 1:
ATGCGCTTTAACAACAAGATGCTGGCGCTGGCCGCTTTACTGTTCGCGGC

ACAGGCTTCGGCGGACACCCTGGAAAGTATCGACAATTGTGCGGTCGGTT

GCCCGACTGGTGGCTCGAGCAATGTGTCGATCGTTCGTCATGCTTATACC

CTTAATAATAACTCGACCACGAAATTCGCTAACTGGGTAGCATATCACAT

TACTAAGGACACTCCGGCCAGCGGTAAGACGCGCAACTGGAAGACCGATC

CGGCGCTCAATCCGGCAGACACCTTAGCACCGGCTGATTATACCGGTGCA

AACGCTGCGCTGAAGGTGGATCGTGGTCACCAGGCGCCGTTGGCATCTCT

GGCTGGTGTAAGCGACTGGGAAAGCCTTAACTATCTCAGCAACATCACCC

CGCAAAAGTCCGACCTGAACCAGGGAGCCTGGGCAGACCTGGAGGACCAA

GAGCGTAAGCTGATTCGTCGGGCCGACATTTCATCGGTCTACACCGTGAC

GGGTCCGCTGTACGAACGTGATATGGGCAAATTACCGGGTACCCAAAAAG

CACACACAATCCCTTCAGCGTATTGGAAAGTCATCTTTATTAATAACTCA

CCAGCGGTTAATCACTATGCTGCATTTCTCTTTGATCAAAATACGCCGAA

AGGGGCAGATTTCTGTCAATTTCGCGTGACCGTTCGTGAGATCGAAAAGC

GGACTGGCCTCATTATTTGGGCCGGCCTGCCGCGTGACGTGCAGGCCTCC

CTGAAGAGTAAACCGGGCGTTCTGCCGGAATTAATGGGCTGTAAGAACGG

GTCAGGGAGTTCCGGTTTGACAACGAACCCGGGGGTGAGTGCTTGGCAGG

TGAACACAGCGTACACCGCTGGTCAGCTGGTGACTTACAATGGTAAAACC

TACAAATGCCTGCAACCACACACTTCACTGGCTGGATGGGAGCCAAGCAA

TGTCCCGGCACTTTGGCAGTTACAGGGGTCTGGTAGCTCGGGACATCACC

ATCATCATCATTAA
```

The single underlined portion of SEQ ID NO: 1 encodes the excretion signal, which is removed in the export of SMN from the whole protein. The double underlined part encodes the CBD portion of the tag, and the dotted underlined part (from the C-terminus) encodes the 6-mer His Tag (SEQ ID NO: 3) with a 6-mer (in this example) Gly-Ser linker.

The DNA in SEQ ID NO: 1, minus the excretion tag portion, encodes the protein in SEQ ID NO: 2:

```
SEQ ID NO: 2:
DTLESIDNCAVGCPTGGSSNVSIVRHAYTLNNNSTTKFANWVAYHITKDT

PASGKTRNWKTDPALNPADTLAPADYTGANAALKVDRGHQAPLASLAGVS

DWESLNYLSNITPQKSDLNQGAWADLEDQERKLIRRADISSVYTVTGPLY

ERDMGKLPGTQKAHTIPSAYWKVIFINNSPAVNHYAAFLFDQNTPKGADF
```

-continued

```
CQFRVTVREIEKRTGLIIWAGLPRDVQASLKSKPGVLPELMGCKNGSGSS

GLTTNPGVSAWQVNTAYTAGQLVTYNGKTYKCLQPHTSLAGWEPSNVPAL

WQLQGSGSSGHHHHHH
```

Again, in SEQ ID NO: 2, the double underlined portion is the CBD portion of the tag, and the dotted underlined part (from the C-terminus) is the 6-mer His Tag with a 6-mer Gly-Ser linker. SMN with CBD/His Tags as shown was expressed extracellularly in C2566 (New England Biolabs, MA) with the plasmid construct as a kanamycin resistant pBAD vector. The enzyme was collected and purified without the step of binding chitin on resin or beads.

Figure 2:
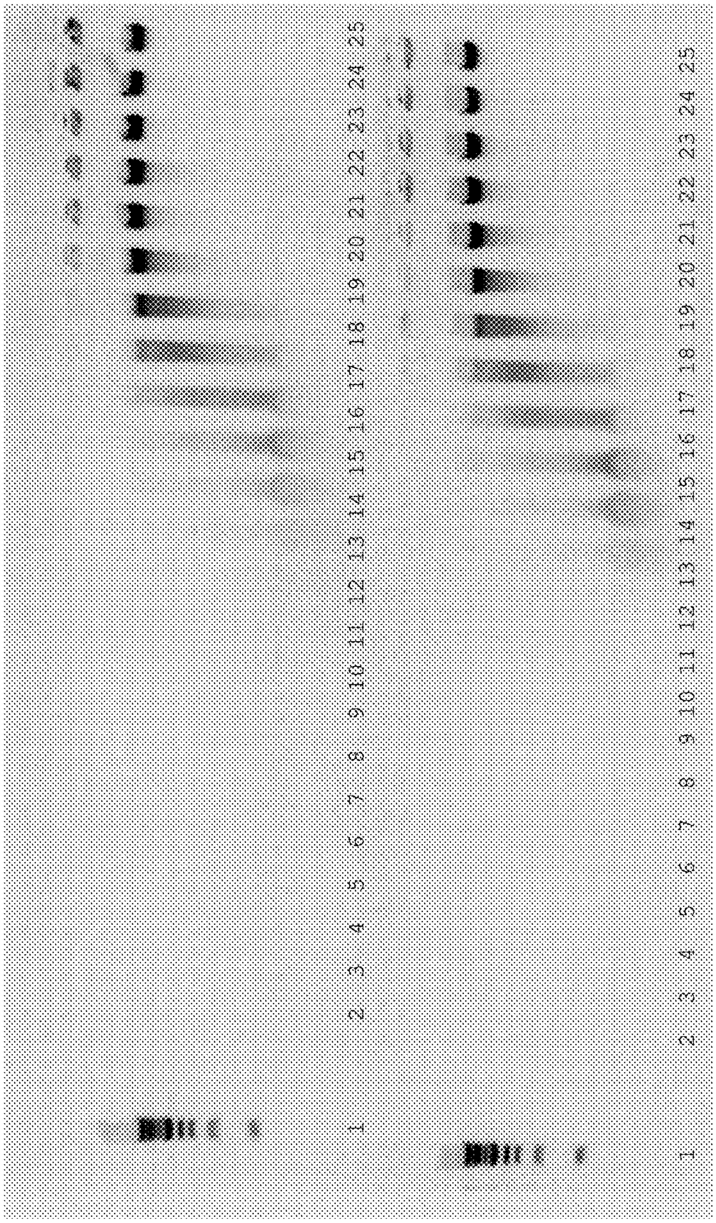
FIG. 2: Confirmation of SMN activity on nucleic acids with and without the addition of tags. The upper panel is recombinant SMN (with the CBD/6-mer His tags), and the bottom panel is SMN without any tags. Lane 1 on each panel is the 1 kb DNA ladder from New England Biolabs, Ipswich, MA; lanes 2 to 25 represent a 2-fold serial dilution of the SMN, with 0.2 μg lambda DNA (dam-), in pH 8.0, 10 mM Tris-HCl, 2 mM $MgCl_2$, incubated 30 minutes at 37° C. Reactions were stopped with a dye solution containing GelRed Nucleic acid stain and were run on 0.8% agarose gel for 20 minutes at 200 V.
Figure 3:
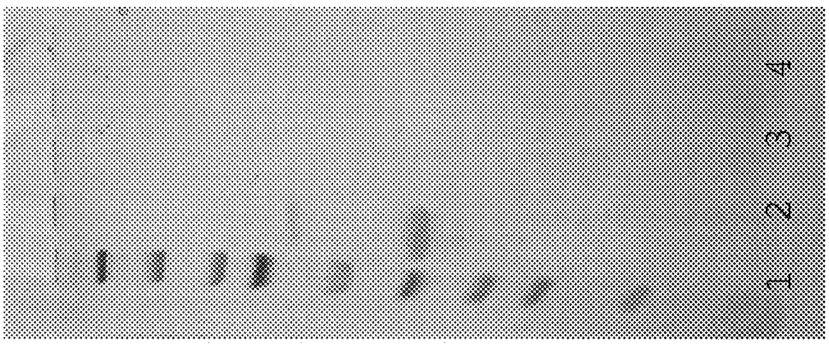
FIG. 3: Bis-tris protein gel of the recombinant SMN (with CBD/6-mer His tags) confirming the binding capability to nickel magnetic beads or chitin magnetic beads. Lane 1 is the ColorMixed Protein Marker 180 (10-180 kDa) protein marker (ABclonal, Woburn MA); Lane 2 is 2.8 μg purified SMN with CBD/6-mer; Lane 3 shows a sample of recombinant SMN (with CBD/6-mer His tags) after incubation with 10 μl nickel magnetic beads; and Lane 4 is a sample of recombinant SMN (with CBD/6-mer His tags) after incubation with 10 μl of chitin magnetic beads.

SMN activity was assayed with the purified protein on lambda DNA, using SMN without tags as the activity reference in the same molar concentration. Lambda DNA was digested into smear first, then to fragments of 1 to 4 nucleotides. The starting molar concentration is 1 µM. As shown in FIG. 2, the digestion pattern of SMN without tags and that of SMN with the CBD/6-mer His-tag are very similar, indicating that the presence of the added tags does not reduce enzyme activity. To confirm binding capability, 2.8 µg of SMN tagged with CBD/6-mer His was incubated with either Nickel magnetic beads or Chitin magnetic beads. As shown in FIG. 3, lanes 3 and 4, either nickel magnetic beads or Chitin magnetic beads can efficiently remove the SMN with a CBD/6-mer His-tag from the solution.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, including but not limited to Variant Sequences, and that such modifications and variations are considered to be within the scope of this invention as defined by the appended claims.

SEQUENCE LISTING

```
Sequence total quantity: 3
SEQ ID NO: 1           moltype = DNA  length = 1014
FEATURE                Location/Qualifiers
source                 1..1014
                       mol_type = other DNA
                       organism = synthetic construct
SEQUENCE: 1
atgcgcttta acaacaagat gctggcgctg gccgctttac tgttcgcggc acaggcttcg  60
gcggacaccc tggaaagtat cgacaattgt gcggtcggtt gcccgactgg tggctcgagc  120
aatgtgtcga tcgttcgtca tgcttatacc cttaataata actcgaccac gaaattcgct  180
aactgggtag catatcacat tactaaggac actccggcca gcggtaagac gcgcaactgg  240
aagaccgatc cggcgctcaa tccggcagac accttagcac cggctgatta taccggtgca  300
aacgctgcgc tgaaggtgga tcgtggtcac caggcgccgt tggcatctct ggctggtgta  360
agcgactggg aaagccttaa ctatctcagc aacatcaccc cgcaaaagtc cgacctgaac  420
cagggagcct gggcagacct ggaggaccaa gagcgtaagc tgattcgtcg ggccgacatt  480
tcatcggtct acaccgtgac gggtccgctg tacgaacgtg atatgggcaa attaccgggt  540
acccaaaaag cacacacaat cccttcagcg tattggaaag tcatctttat taataactca  600
ccagcggtta atcactatgc tgcatttctc tttgatcaaa atacgccgaa aggggcagat  660
ttctgtcaat ttcgcgtgac cgttcgtgag atcgaaaagc ggactggcct cattatttgg  720
gccggcctgc cgcgtgacgt gcaggcctcc ctgaagagta aaccgggcgt tctgccggaa  780
ttaatgggct gtaagaacgg gtcagggagt tccggtttga caacgaaccc gggggtgagt  840
gcttggcagg tgaacacagc gtacaccgct ggtcagctgg tgacttacaa tggtaaaacc  900
tacaaatgcc tgcaaccaca cacttcactg gctggatggg agccaagcaa tgtcccggca  960
ctttggcagt tacaggggtc tggtagctcg ggacatcacc atcatcatca ttaa        1014

SEQ ID NO: 2           moltype = AA  length = 316
FEATURE                Location/Qualifiers
source                 1..316
                       mol_type = protein
                       organism = synthetic construct
SEQUENCE: 2
DTLESIDNCA VGCPTGGSSN VSIVRHAYTL NNNSTTKFAN WVAYHITKDT PASGKTRNWK  60
TDPALNPADT LAPADYTGAN AALKVDRGHQ APLASLAGVS DWESLNYLSN ITPQKSDLNQ  120
GAWADLEDQE RKLIRRADIS SVYTVTGPLY ERDMGKLPGT QKAHTIPSAY WKVIFINNSP  180
AVNHYAAFLF DQNTPKGADF CQFRVTVREI EKRTGLIIWA GLPRDVQASL KSKPGVLPEL  240
MGCKNGSGSS GLTTNPGVSA WQVNTAYTAG QLVTYNGKTY KCLQPHTSLA GWEPSNVPAL  300
WQLQGSGSSG HHHHHH                                                  316

SEQ ID NO: 3           moltype = AA  length = 6
FEATURE                Location/Qualifiers
source                 1..6
                       mol_type = protein
                       organism = synthetic construct
SEQUENCE: 3
HHHHHH                                                             6
```

What is claimed is:

1. A mutant *Serratia Marcescens* Nuclease having the amino acid sequence of SEQ ID NO: 2 bound to a nickel magnetic bead through the Chitin Binding Domain tag of SEQ ID NO: 2.

* * * * *